US 6,682,558 B2

(12) United States Patent
Tu et al.

(10) Patent No.: US 6,682,558 B2
(45) Date of Patent: Jan. 27, 2004

(54) DELIVERY SYSTEM FOR A STENTLESS VALVE BIOPROSTHESIS

(75) Inventors: Hosheng Tu, Tustin, CA (US); Rodolfo C. Quijano, Laguna Hills, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 48 days.

(21) Appl. No.: 09/853,463

(22) Filed: May 10, 2001

(65) Prior Publication Data

US 2002/0169456 A1 Nov. 14, 2002

(51) Int. Cl.[7] ................................................ A61F 2/06
(52) U.S. Cl. ....................................................... 623/2.11
(58) Field of Search .................... 623/2.1, 2.11, 623/2.12, 2.13, 2.15, 2.16, 1.24, 1.26, 1.11, 1.23; 606/108

(56) References Cited

U.S. PATENT DOCUMENTS

| 4,056,854 A | * | 11/1977 | Boretos et al. ............. 128/899 |
| 4,960,424 A | * | 10/1990 | Grooters ..................... 128/898 |
| 5,064,435 A | | 11/1991 | Porter |
| 5,197,979 A | | 3/1993 | Quintero et al. |
| 5,489,297 A | | 2/1996 | Duran |
| 5,545,214 A | * | 8/1996 | Stevens ....................... 128/898 |
| 5,554,185 A | * | 9/1996 | Block et al. ................. 606/195 |
| 5,840,081 A | | 11/1998 | Andersen et al. |
| 5,895,420 A | | 4/1999 | Mirsch, II et al. |
| 5,935,163 A | | 8/1999 | Gabbay |
| 6,168,614 B1 | | 1/2001 | Andersen et al. |
| 6,287,334 B1 | * | 9/2001 | Moll et al. .................. 128/898 |

FOREIGN PATENT DOCUMENTS

| WO | WO 99/33412 | 7/1999 |
| WO | WO 00/00107 | 1/2000 |

OTHER PUBLICATIONS

Georg Lutter et al, "Percutaneous Transluminal Replacement of the Aortic Valve" 81st Annual Meeting AATS, p. 174, May 6–9, 2001 San Diego, CA.

* cited by examiner

Primary Examiner—Corrine McDermott
Assistant Examiner—William H. Matthews
(74) Attorney, Agent, or Firm—Jones Day (57) ABSTRACT

The current invention discloses a catheter and a method for delivering a stentless bioprosthesis in a body channel, the method comprising percutaneously introducing a catheter into the body channel, wherein the catheter contains said stentless bioprosthesis at a retracted state; and disengaging said stentless bioprosthesis out of a distal opening of the catheter by a pulling mechanism associated with the catheter structure.

7 Claims, 7 Drawing Sheets

DELIVERY SYSTEM FOR A STENTLESS VALVE BIOPROSTHESIS

TECHNICAL FIELD OF INVENTION

The present invention generally relates to a tubular prosthesis and methods for delivery into a body channel. More particularly, the present invention relates to an improved delivery system for delivering a stentless bioprosthesis comprising a collapsible elastic valve or a biological graft at a desired anatomical site of the body channel for implantation.

BACKGROUND OF THE INVENTION

A prosthetic heart valve may be used to replace a diseased natural heart valve in a human patient. Similarly, a prosthetic venous valve may be used to replace a dysfunctional natural venous valve in a patient. Mechanical heart valves typically have a rigid orifice ring and rigid hinged leaflets coated with a blood compatible substance such as pyrolytic carbon. Other configurations, such as ball-and-cage assemblies, have also been used for such mechanical valves. A mechanical heart valve cannot be retracted radially and delivered by a catheter-based delivery system.

In contrast to mechanical heart valves, bioprosthetic heart valves comprise valve leaflets formed of biological material. Many bioprosthetic valves include a support structure, or stent, for supporting the leaflets and maintaining the anatomical structure of the valve. Stented bioprosthetic valves generally are prepared by chemically cross-linking a retrieved pig's heart valve, followed by attaching it to a stent. The stent provides structural support to the valve and, with a sewing cuff, facilitates attachment of the valve to the patient by suturing. Gabbay in U.S. Pat. No. 5,935,163 discloses a natural tissue heart valve prosthesis with a substantially flexible annular ring to provide additional support, the entire contents of which are incorporated herein by reference.

One of the major functions of stents is to serve as a framework for attachment of the valve and for suturing the valve into place in the human patient. Various stent designs have been implemented in a continuing effort to render valve implantation simpler and more efficient. Inevitably, however, a stent limits interactions with aortic wall dynamics and tends to inhibit natural valve movement. This results in post-operative transvalvular gradients with resultant additional work burden on the heart. In addition, a stent causes a reduction in size of the bioprosthetic valve that can be placed in a particular location, since the stent and sewing cuff occupy space that otherwise would be available for blood flow. Recently biodegradable stents are disclosed, for example, U.S. Pat. No. 5,895,420 to Mirsch II, et al. and U.S. Pat. No. 5,489,297 to Duran, to limit disadvantage of the valve stenting to a shorter time of implantation until it is biodegraded. Both patents are incorporated herein by reference.

Some bioprosthetic valve manufacturers have attempted to develop methods and systems to ease the implantation of stented valves, including special catheter-based delivery system. Both of U.S. Pat. Nos. 5,840,081 and 6,168,614 to Andersen et al. disclose a minimally invasive percutaneous delivery system with a balloon catheter. A stented valve prosthesis is contractively mounted within a lumen of the catheter during delivery. At a desired anatomical site, the prosthesis is pushed out of the catheter tip and self expands. Lutter et al. reported an experimental study on percutaneous transluminal replacement of the aortic valve ($81^{st}$ American Association for Thoracic Surgery Program Book pp. 174, May 6–9, 2001, San Diego, Calif.). They concluded that aortic valve stents with a self-expandable metallic stent can be successfully implanted by transluminal catheter technique without the need of opening the chest.

Porter in U.S. Pat. No. 5,064,435 discloses a catheter-based apparatus and methods for releasing a self-expandable prosthesis by a conventional pushing mechanism. The above-mentioned approaches are satisfactory for delivering a stented prosthesis having an external rigid support adapted for receiving the pushing force. A self-expanding prosthesis often is preferred over a plastically deformed device. Resilient prosthesis can be deployed without dilatation balloons or other stent expanding means. A self-expanding prosthesis can be preselected in accordance with the diameter of the body channel or other anatomic site for fixation. While deployment requires skill in positioning the prosthesis, the added skill of properly dilating the balloon to plastically expand a prosthesis to a selected diameter is not required. Also, the self-expanding prosthesis remains at least slightly compressed after fixation, and thus has a restoring force which facilitates acute fixation.

Stentless valves have demonstrated better hemodynamic function than stented valves. This is because a stentless valve is sewn directly into the host tissues, without the need for extraneous structure such as a sewing cuff. Such extraneous structures inevitably compromise hemodynamics. A stentless valve closely resembles a native valve in its appearance and function, and rely upon the patient's tissues to supply the structural support normally provided by a stent. Quintero et al. in U.S. Pat. No. 5,197,979, NguyenThien-Nhon in PCT W.O. No. 99/33412, and Vrandecic Peredo in PCT W.O. No. 00/00107 all disclose stentless valve structure and function, the entire contents of which are incorporated herein by reference.

The main disadvantage to stentless valves has been in their difficulty of deployment and implantation, particularly in a catheter-based percutaneous route. With recent scientific advancements in robotics, instrumentation and computer technology, a minimally invasive catheter-based delivery system for a stentless bioprosthesis is imminent. There is currently a clinical need for deploying a tubular stentless prosthesis, such as a stentless valve or a vascular graft without a rigid support, into a body channel, preferably by a percutaneous approach. The catheter-based percutaneous delivery system as compared to an open-cavity surgery will greatly reduce the patient's hospital stay and improve recovery.

SUMMARY OF THE INVENTION

It is an object of the present invention to provide a method for delivering a stentless bioprosthesis in a body channel, the method comprising percutaneously introducing a catheter into the body channel, wherein the catheter contains the radially elastic stentless bioprosthesis at a retracted state; and disengaging said stentless bioprosthesis out of a distal opening of the catheter by a pulling mechanism. In one embodiment, the pulling mechanism further comprises an engaging element coupling to a distal portion of the stentless bioprosthesis. In another embodiment, the method further comprises separating the stentless bioprosthesis from said engaging element.

The stentless bioprosthesis of the present invention has the common characteristics of soft, collapsible radially, collapsible longitudinally, and without any rigid support onto or around the bioprosthesis.

It is another object of the present invention to provide a catheter for delivering a tubular prosthesis to an anatomical site in a body channel, the catheter comprising an elongated delivery member located inside the lumen of the catheter, the elongated delivery member having an engaging element at the distal end of the elongated delivery member, wherein the engaging element is adapted for engaging and disengaging a distal portion of the tubular prosthesis. In one embodiment, the catheter further comprises a delivery mechanism at the handle that is coupled to the elongated delivery member. The delivery mechanism is adapted for pulling the distal portion of the tubular prosthesis out of the catheter shaft during a deployment or releasing stage. In another embodiment, the engaging element comprises a plurality of releasable sutures, gripping jaws or bioadhesives.

It is still another object of the present invention to provide a method for delivering a tubular stentless prosthesis to an anatomical site in a body channel, the method comprising the steps of introducing a catheter into the body channel, wherein the catheter contains the tubular stentless prosthesis at a retracted state; advancing the catheter to the anatomical site; maintaining a distal portion of the tubular stentless prosthesis in place relative to the anatomical site; disengaging the catheter from the tubular stentless prosthesis adapted for self-expanding said prosthesis from the retracted state; and withdrawing said catheter from the body channel The tubular stentless prosthesis of the present invention generally includes, but not limited to, a vascular graft, a synthetic vascular graft, a biological vascular graft, a cardiac valve, a valved conduit, a venous valve, and other stentless implantable devices. The "tubular stentless prosthesis" is essentially synonymous with the "longitudinally collapsible prosthesis" in the invention.

In a further embodiment, the method comprises another step of coupling the prosthesis into tissue of the body channel, wherein the coupling means may include stapling, adhering, stenting, anchoring and the like.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is an embodiment of the device delivery system and methods, comprising a delivery catheter adapted particularly for delivering a tubular stentless prosthesis to an anatomical site in a body channel.

Figure 1:
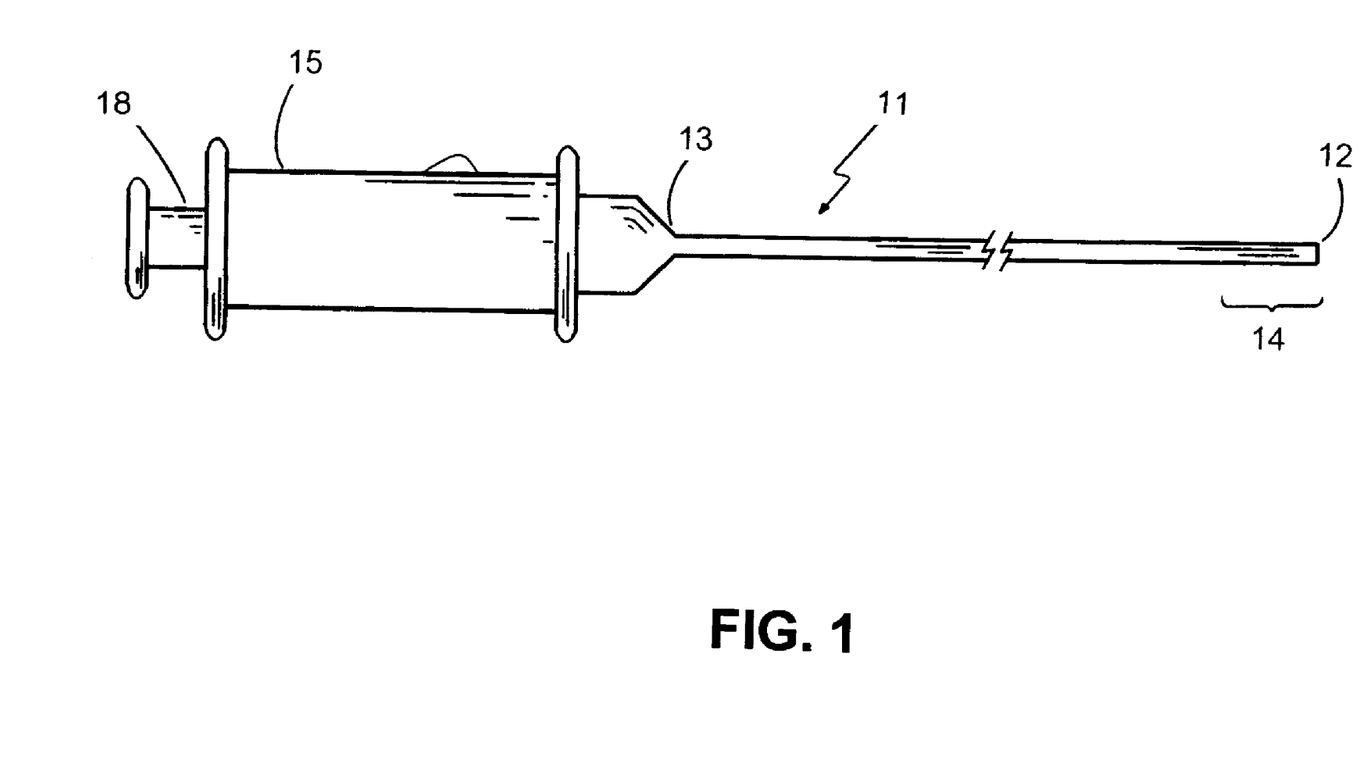
FIG. 1 is an overall view of a delivery catheter of the present invention for delivering a tubular stentless prosthesis into a body channel.

FIG. 1 shows an overall view of a delivery catheter of the present invention for delivering a tubular stentless prosthesis into a body channel. A tubular stentless prosthesis is a prosthesis without a support or stent. Typically such a prosthesis is soft, flexible and very compressible or collapsible either radially or longitudinally. The best handling method is to hold it in its natural position without buckling, compression, or "spaghetti-like" twisting. When such a prosthesis 31 is held horizontally, the best way to move it in an essentially straight manner is to pull the distal section 32 forward rather than push its proximal end 33.

The catheter 11 of the present invention comprises a catheter shaft 17, the catheter shaft having a distal end 12, a distal opening 16, a proximal end 13, and a lumen 22 between the distal end 12 and the proximal end 13. The catheter also comprises a distal section 14 that is used to hold the retracted prosthesis 31B during the catheter delivery stage. A fully un-retracted (free from constraint) prosthesis 31 in the present invention is the one prior to being inserted into the lumen 22 or after fully deployed/released from the lumen.

The catheter also comprises a handle 15 that is attached to the proximal end 13 of the catheter shaft 17. There is an elongated delivery member 21 located inside said lumen 22 (see FIG. 2), wherein the delivery member can be deployed forward or backward axially. The elongated delivery member has an engaging element 35A, 35B at a distal end 26 of the elongated delivery member 21, wherein the engaging element 35A, 35B is adapted for engaging and disengaging a distal portion 32 of said tubular prosthesis 31B (see FIG. 3). The tubular prosthesis is characterized by its softness and collapsibility radially and/or longitudinally.

The engaging element may comprise a plurality of releasable sutures, wherein the sutures may be released from the engaging element by, for example a cutting instrument. The engaging element may also comprise a plurality of releasably gripping jaws, wherein the gripping jaws may be released after the stentless prosthesis is deployed into place. Further, the engaging element may comprise a plurality of heat-disengageable wires, for example the fuse-like safety wires. A moderate heat can be provided through radiofrequency, ultrasound, electromagnetic or the like to disengage the wires from the prosthesis.

The catheter further comprises a delivery mechanism 18 at the handle 15, the delivery mechanism 18 is coupled to the elongated delivery member 21, wherein the delivery mechanism 18 is adapted for pulling the distal portion 32 of the tubular prosthesis 31B out of the catheter shaft 17 during a prosthesis releasing stage.

The catheter of the present invention may be in the 8 French to 20 French size in diameter. However, the dimension outside this range is also applicable depending on the anatomic site and application. The material for catheters is generally biocompatible and flexible for inserting purposes.

The method for delivering a tubular stentless prosthesis 31 to an anatomical site in a body channel may comprise several major steps of (a) introducing a catheter into the body channel, wherein the catheter contains the tubular stentless prosthesis at a retracted state; (b) advancing the catheter to the anatomical site; (c) maintaining a distal portion of said tubular stentless prosthesis in place relative to the anatomical site; (d) disengaging the catheter from the tubular stentless prosthesis adapted for self-expanding said prosthesis from the retracted state; and (e) withdrawing the catheter from the body channel.

Figure 2:
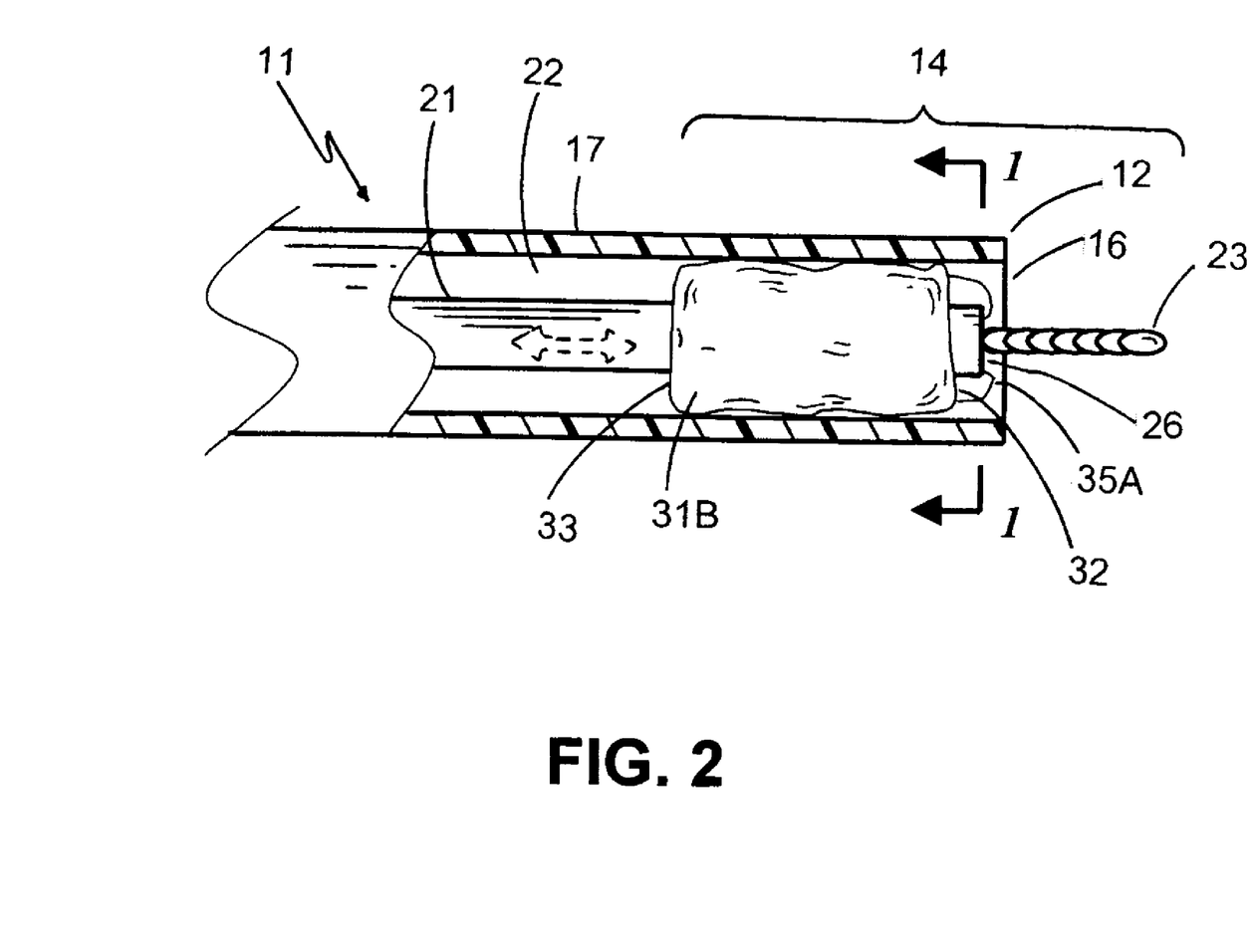
FIG. 2 is an enlarged distal portion view of the catheter showing a first stage of the delivery sequences in accordance to the principles of the present invention.

FIG. 2 shows an enlarged distal portion 14 of the catheter 11 showing a first stage of the delivery sequences in accordance to the principles of the present invention. A tubular stentless prosthesis 31 can be crimped, compressed, constricted, constrained, contracted, or retracted radially to form a retracted prosthesis 31B so as to snugly fit into a narrow lumen 22 of the catheter shaft 17 at its distal section for delivering to the anatomical site.

Figure 2A:
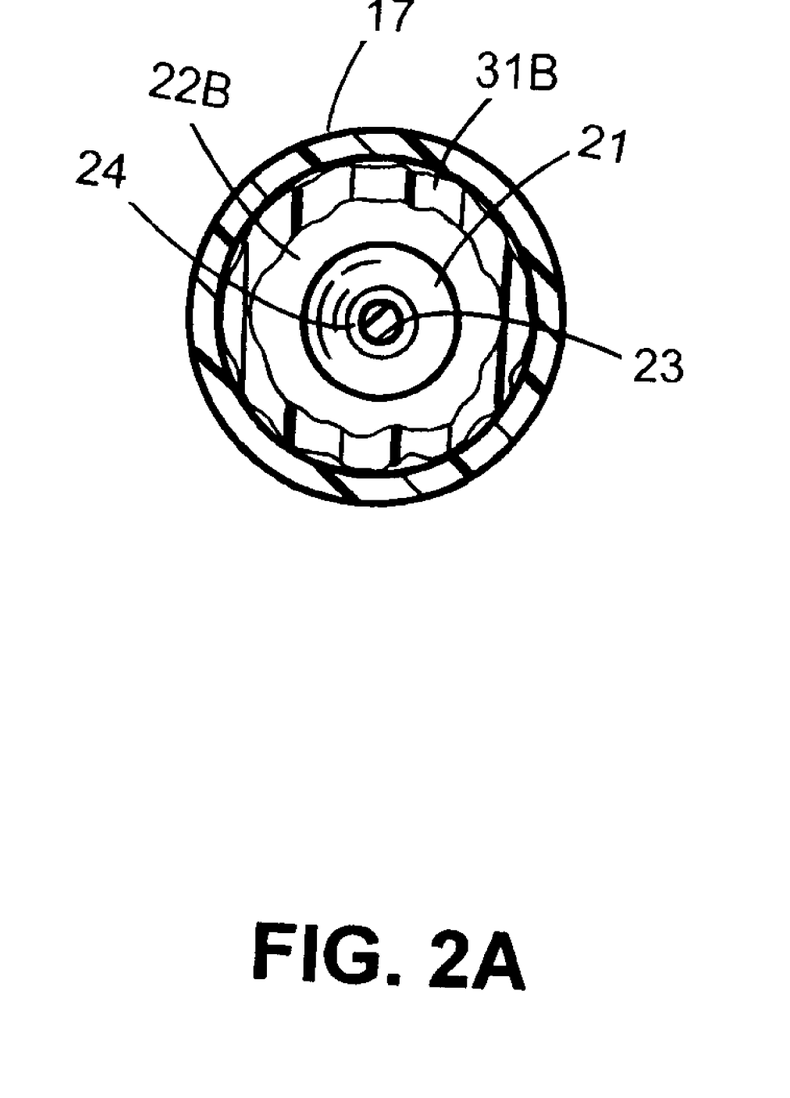
FIG. 2A is a transverse view of the section 1—1 of FIG. 2 showing the relative location of the catheter shaft and the prosthesis inside the shaft.

FIG. 2A shows a transverse view of the section 1—1 of FIG. 2 showing the relative location of the catheter shaft 17 and the prosthesis 31B inside the shaft. The catheter has an optional guidewire lumen or channel for riding the catheter shaft over a guidewire 23. In one embodiment, the guidewire lumen 24 is provided within the elongated delivery member 21. In another embodiment, the guidewire channel is provided at the distal section of the catheter shaft as a rapid exchange type guidewire system. The guidewire lumen is adapted for introducing a guidewire of about 0.014 inch or smaller.

Figure 3:
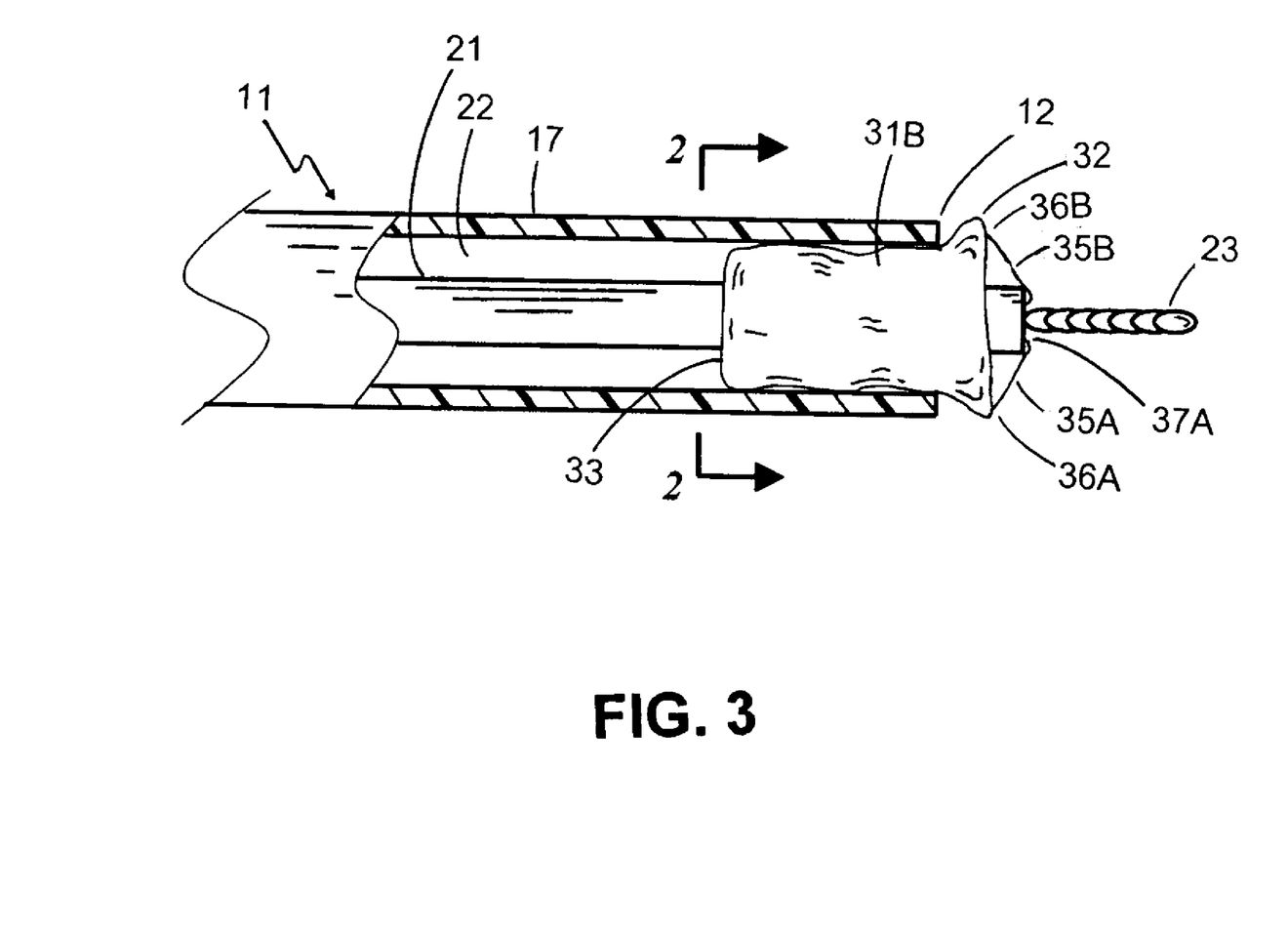
FIG. 3 is an enlarged distal portion view of the catheter showing a second stage of the delivery sequences in accordance to the principles of the present invention.

FIG. 3 shows an enlarged distal portion 14 view of the catheter showing a generally second stage of the delivery sequences in accordance to the principles of the present invention. The distal portion 32 of the prosthesis 31B is pulled out of the distal opening 16 of the catheter shaft 17 by a pulling action from the distal end of the elongated delivery member 21. In one embodiment, the pulling action is accomplished by an engaging element, wherein the engaging element 35A, 35B may have its engaging points 37A, 37B at the distal end 26 of the elongated delivery member 21 and another engaging points 36A, 36B at the distal section 32 of the prosthesis 31B. In a relative sense when the distal section 32 remains fixed relative to an anatomical site, the catheter 11 is viewed as moving backward toward the operator. The distal portion 32 of the prosthesis 31B self-expands radially due to its elastic feature when the constraint is removed.

To ensure that the self-expanded prosthesis will stay at a desired anatomic site within the body channel, the method may further comprise a step of coupling the prosthesis into tissue of the body channel whenever feasible. The coupling method may include stapling, adhering by a bio-adhesive, such as Bio-glue™ (from CryoLife, Inc., Kennesaw, Ga., USA). The stapling step may include stapling both the distal portion and the proximal portion of the prosthesis into tissue of the body channel, though more than two stapling points is also applicable.

Figure 3A:
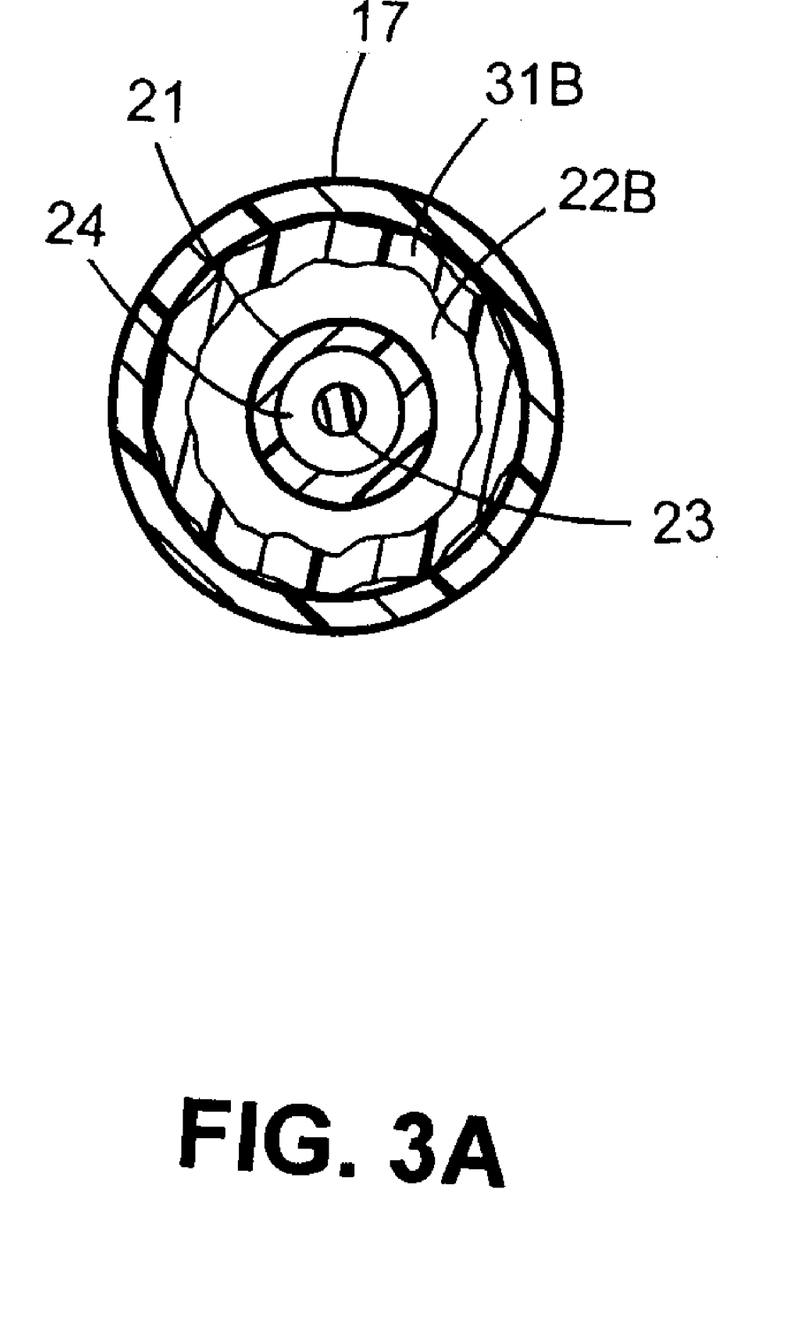
FIG. 3A is a transverse view of the section 2—2 of FIG. 3 showing the relative location of the catheter shaft and the prosthesis inside the shaft.

FIG. 3A shows a transverse view of the section 2—2 of FIG. 3 showing the relative location of the catheter shaft 17 and the prosthesis 31B inside the shaft. In a preferred embodiment, the guidewire lumen 24 is provided within the elongated delivery member 21 of the catheter 11 for riding the catheter shaft over a guidewire 23.

Figure 4:
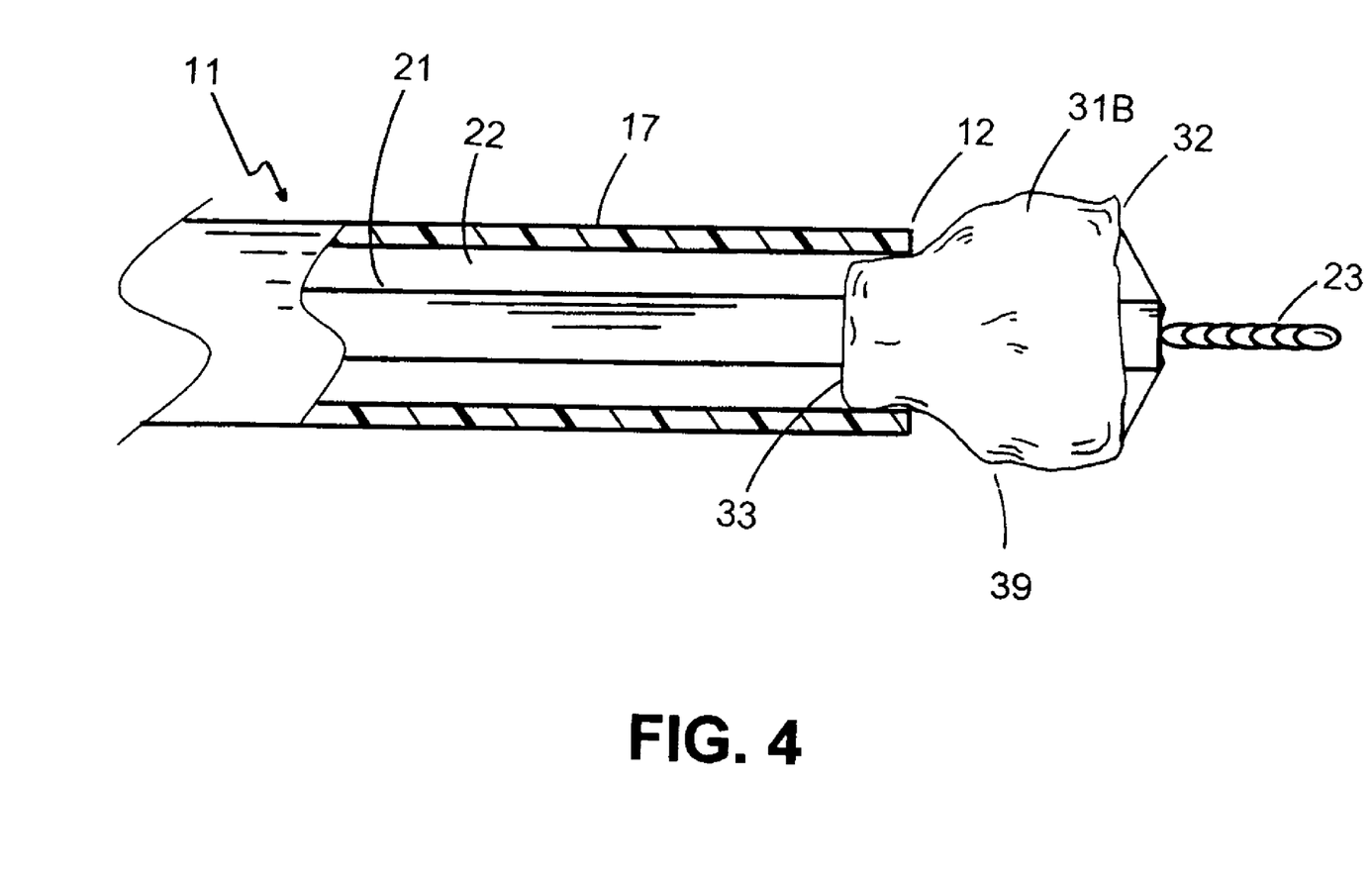
FIG. 4 is an enlarged distal portion view of the catheter showing a third stage of the delivery sequences in accordance to the principles of the present invention.

FIG. 4 shows an enlarged distal portion 14 view of the catheter showing a generally third stage of the delivery sequences in accordance to the principles of the present invention. The majority of the prosthesis 31B is pulled out of the distal opening 16 of the catheter shaft 17 by a pulling action from the distal end of the elongated delivery member 21. At this stage, the distal portion 32 and the middle portion 39 of the prosthesis 31B self-expands radially due to its elastic feature when the constraint is removed.

Figure 5:
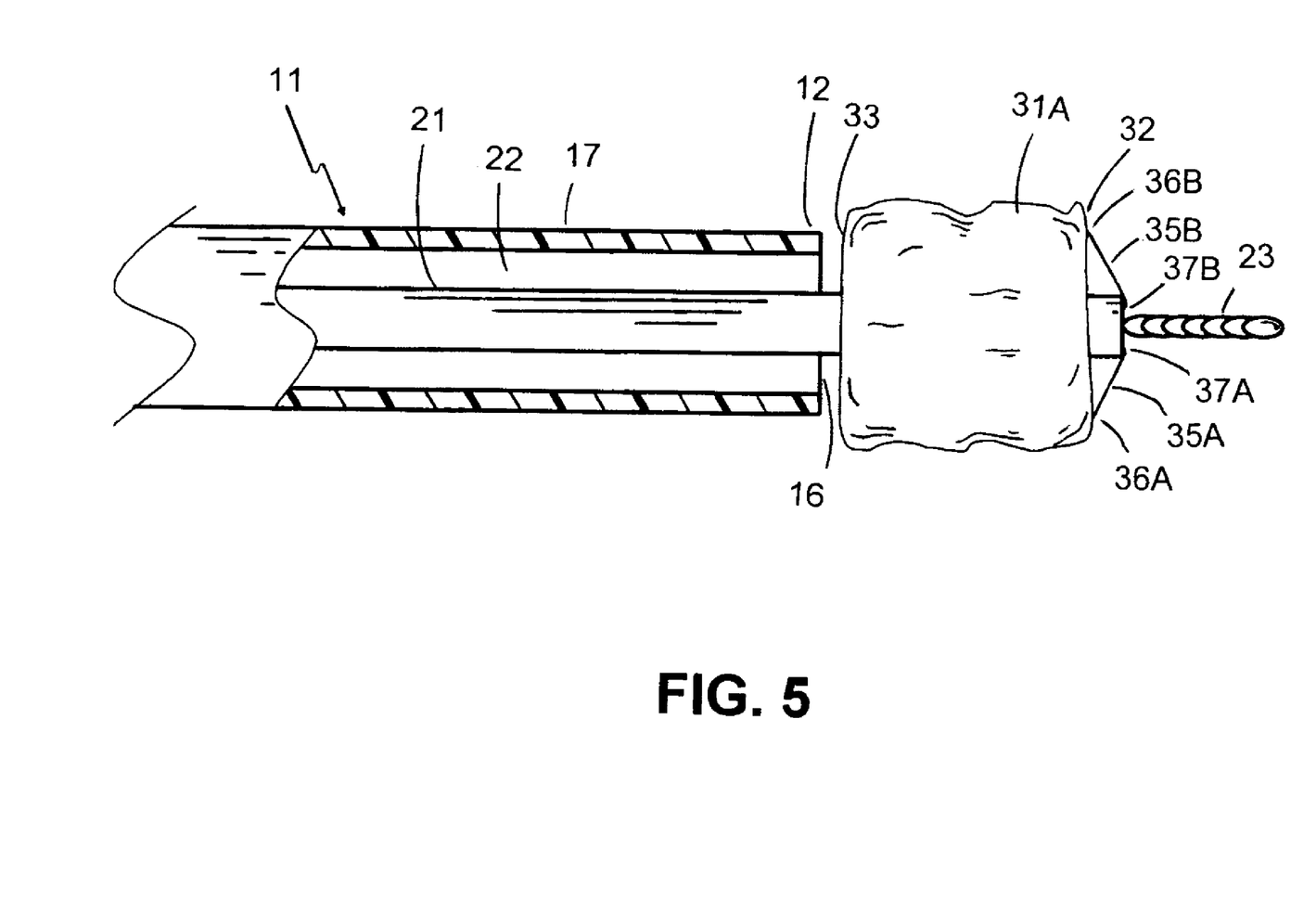
FIG. 5 is an enlarged distal portion view of the catheter showing a fourth stage of the delivery sequences in accordance to the principles of the present invention.

FIG. 5 shows an enlarged distal portion 14 view of the catheter showing a generally fourth stage of the delivery sequences in accordance to the principles of the present invention. The whole prosthesis 31A is pulled out of the distal opening 16 of the catheter shaft 17 by a pulling action from the distal end 26 of the elongated delivery member 21. At this stage, the distal portion 32, the middle portion 39, and the proximal end 33 of the prosthesis 31B self-expands radially to form the unconstrained prosthesis 31A as a result of its elastic feature when the constraint is completely removed.

To provide an additional therapeutic therapy to the anatomic site, a therapeutic fluid is introduced into the lumen of the catheter shaft. The therapeutic fluid may be selected from a group consisting of an anti-inflammatory solution, an anti-virus solution, an antibiotic solution, an angiogenic fluid, heparin solution, an anti-sense fluid, an antiangiogenic fluid, a biocompatible adhesive, and a combination thereof. Typically a fluid inlet port is provided at about the handle of the catheter and the fluid can be supplied by a syringe or an infusion pump coupling to the fluid inlet port. The biocompatible adhesive, such as Bio-glue™ (from CryoLife, Inc., Kennesaw, Ga., USA) can be used to adhere the distal section of the longitudinally collapsible prosthesis on to the tissue at the anatomic site.

From the foregoing description, it should now be appreciated that a method for delivering a stentless bioprosthesis in a body channel, the method comprising percutaneously introducing a catheter into the body channel, wherein the catheter contains the stentless bioprosthesis at a retracted state; and disengaging said stentless bioprosthesis out of a distal opening of the catheter by a pulling mechanism has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for delivering a hollow tubular collapsible prosthesis to an anatomical site in a body channel, the method comprising the steps of:
   introducing a catheter into the body channel, wherein the catheter contains said prosthesis at a retracted state;
   advancing the catheter to the anatomical site;
   maintaining a distal portion of said prosthesis in place relative to the anatomical site;
   disengaging said prosthesis from said catheter by pulling a distal end of said prosthesis; and
   withdrawing said catheter from the body channel.

2. The method according to claim 1, wherein the prosthesis is a stentless cardiac valve.

3. The method according to claim 1, wherein the method further comprises a step of coupling said prosthesis into tissue of the body channel.

4. The method according to claim 1, wherein said distal portion of the prosthesis is maintained in place at a position relative to the anatomical site by an elongated delivery member located within a lumen of the catheter, said elongated delivery member having an engaging element at a distal end of said elongated delivery member, wherein the engaging element engages and disengages the distal portion of said prosthesis.

5. A method for delivering a hollow tubular stentless longitudinally collapsible bioprosthesis in a body channel, the method comprising percutaneously introducing a catheter into the body channel, wherein the catheter contains said bioprosthesis at a retracted state; and disengaging said bioprosthesis out of a distal opening of the catheter by pulling at a distal end of said bioprosthesis.

6. The method according to claim 5, wherein said pulling mechanism further comprises an engaging element coupling to a distal portion of the bioprosthesis.

7. The method according to claim 6, wherein the method further comprises separating the bioprosthesis from said engaging element.

* * * * *